United States Patent [19]

Prager

[11] 4,351,322
[45] Sep. 28, 1982

[54] STOMA CONTROL DEVICE AND METHOD

[76] Inventor: Elliot D. Prager, 1685 E. Valley Rd., Santa Barbara, Calif. 93108

[21] Appl. No.: 195,944

[22] Filed: Oct. 10, 1980

[51] Int. Cl.³ .............................................. A61M 19/00
[52] U.S. Cl. ................................... 128/1 R; 128/344
[58] Field of Search ............... 128/1 R, 283, DIG. 25, 128/129, 344

[56] References Cited

U.S. PATENT DOCUMENTS

| | | | |
|---|---|---|---|
| 1,810,466 | 6/1931 | Deutsch | |
| 2,000,683 | 5/1935 | Akitt | |
| 2,243,529 | 5/1941 | Grossman et al. | |
| 2,324,520 | 7/1943 | Lamson | 128/1 R |
| 2,494,393 | 1/1950 | Lamson | |
| 2,510,766 | 6/1950 | Surface | |
| 2,564,399 | 8/1951 | Franken | 128/1 R |
| 2,703,576 | 3/1955 | Furr, Jr. | |
| 2,931,353 | 4/1960 | Kitzul | |
| 3,083,704 | 4/1963 | Swearingen | |
| 3,216,420 | 11/1965 | Smith et al. | |
| 3,253,594 | 5/1966 | Matthews et al. | |
| 3,293,663 | 12/1966 | Cronin | |
| 3,447,533 | 6/1969 | Spicer | |
| 3,565,073 | 2/1971 | Glesy | 128/283 |
| 3,799,166 | 3/1974 | Marsan | 128/283 |
| 3,802,418 | 4/1974 | Clayton | 128/2 F |
| 3,805,789 | 4/1974 | Marsan | 128/283 |
| 3,827,435 | 8/1974 | Marsan | 128/283 |
| 3,828,782 | 8/1974 | Polin | 128/283 |
| 3,841,304 | 10/1974 | Jones | 128/1 R |
| 3,875,928 | 4/1975 | Angelchik | 128/1 R |
| 3,877,431 | 4/1975 | Kross | 128/283 |
| 3,878,847 | 4/1975 | Marsan | 128/283 |
| 3,897,780 | 8/1975 | Trousil | 128/283 |
| 3,897,781 | 8/1975 | Marsan | 128/283 |
| 3,902,496 | 9/1975 | Eakin | 128/283 |
| 3,906,951 | 9/1975 | Chen James Ling | 128/283 |
| 3,938,521 | 2/1976 | Ritota et al. | 128/283 |
| 3,941,133 | 3/1976 | Chen | 128/283 |
| 3,948,256 | 4/1976 | Schneider | 128/283 |
| 3,952,726 | 4/1976 | Hennig et al. | 128/1 R |
| 3,952,727 | 4/1976 | Nolan | 128/283 |
| 3,958,556 | 5/1976 | Schenk | 128/1 R |
| 3,970,085 | 7/1976 | Mersan | 128/283 |
| 3,980,084 | 9/1976 | Kross | 128/283 |
| 3,986,213 | 10/1976 | Lynch | 3/36 |
| 4,019,499 | 4/1977 | Fitzgerald | 128/1 R |
| 4,067,335 | 1/1978 | Silvanov | 128/283 |
| 4,078,568 | 3/1978 | Etes et al. | 128/283 |
| 4,100,627 | 7/1978 | Brill | 3/36 |
| 4,117,847 | 10/1978 | Clayton | 128/348 |
| 4,119,100 | 10/1978 | Rickett | 128/350 R |
| 4,121,589 | 10/1978 | McDonnell | 128/283 |
| 4,137,918 | 2/1979 | Bogert | 128/283 |
| 4,153,055 | 5/1979 | Etes | 128/156 |
| 4,154,226 | 5/1979 | Hennig et al. | 128/1 R |
| 4,166,051 | 8/1979 | Cilento et al. | 260/17.4 |
| 4,167,952 | 9/1979 | Reinicke | 137/493 |
| 4,170,231 | 10/1979 | Collins | 128/283 |
| 4,183,357 | 1/1980 | Bentley et al. | 128/283 |
| 4,185,630 | 1/1980 | Neumeier et al. | 128/283 |
| 4,187,850 | 2/1980 | Gust | 128/283 |
| 4,192,785 | 3/1980 | Chen et al. | 260/17.4 GC |
| 4,194,506 | 3/1980 | Voorhies | |
| 4,209,010 | 6/1980 | Ward et al. | 128/1 R |
| 4,241,735 | 12/1980 | Chernov | 128/344 |

FOREIGN PATENT DOCUMENTS

| | | | |
|---|---|---|---|
| 2206608 | 8/1972 | Fed. Rep. of Germany | |
| 2431888 | 1/1976 | Fed. Rep. of Germany | 128/1 R |
| 2558521 | 6/1977 | Fed. Rep. of Germany | |
| 2740682 | 3/1979 | Fed. Rep. of Germany | |
| 2747245 | 4/1979 | Fed. Rep. of Germany | |
| 2811383 | 9/1979 | Fed. Rep. of Germany | |
| 2380022 | 10/1978 | France | 128/DIG. 25 |
| 2000683 | 6/1978 | United Kingdom | |
| 2007983 | 12/1978 | United Kingdom | |

OTHER PUBLICATIONS

"Artificial Control of Fecal Incontinence", Theodore H. Stanley, M.D., *SURGERY*, Nov. 1970, vol. 68; No. 5, pp. 852-856.

"A Continent Colostomy: The Magnetic Stoma Cap", *The American Journal of Surgery*, vol. 134, Sep. 1977, pp. 334-337.

"The Ostomies, Helping Your Ostomate Patient Cope", *PATIENT CARE* Feb. 20, 1972.

"Continent Colostomy with the Aid of a Magnet Closing System: A Preliminary Report", Jan Kewentor, M.D., *American Society of Colon and Rectal Surgeons*, Div. Col. & Rect., Jun.-Feb. 1973.

"Continent Ileostomy in the Pediatric Patient", I. M.

Gelernt et al., *Journal of Pediatric Surgery*, vol. II, No. 5, (Oct.) 1976.

"Ileostomy with Ileal Reservoir Rather Than Ileostomy Alone", Beahrs et al., *Ann. Surg.*, May 1974.

"The Surface Colostomy Control Button", Tenney and Graney, *American Society of Colon and Rectal Surgeons, Div. Col. & Rect.*, Oct. 1978, pp. 524-533.

"The Quest for Continence A Morphologic Survey of Approaches to a Continent Colostomy", Tenney et al., *Div. Col. & Rec.*, vol. 21, No. 7, 1978, pp. 522-523.

"An Artificial Sphincter: A Preliminary Report", Heildom et al., *Div. Col. & Rect.*, Nov. Dec. 1978, pp. 562-566.

"Artificial Control of the Anal Colostomy in Sheep", Stanley et al., *Journal of Surgical Research*, vol. 9, No. 4, Apr. 1979, pp. 223-227.

"The Kock Pouch: A Continent Ileostomy With No Appliance", W. W. H. Rudd, M.D., *Ostomy Quarterly/*Fall 1977, pp. 4, 6, 7, 23.

"The Continent Ileostomy in the Pediatric Patient", Gelernt et al., *Hospital Practice*, Apr. 1977, pp. 64-74.

"The Continent Reservoir Ileostomy: Review of a Collective Series of Thirty-Six Patients from Three Surgical Departments", Halvorsen et al., *SURGERY*, Mar. 1978, vol. 83, No. 3, pp. 252-258.

"Creating an Ileal Reservoir With a Continent Ileostomy", Oliver H. Beahrs, M., *CONTEMPORARY SURGERY*, vol. 8, Jun. 1976.

"Present Status of the Continent Ileostomy", Symposium *Div. Col. & Rect.*, Apr. 1976, vol. 19, No. 3, pp. 189-190.

"Continent Ileostomy A Compilation of Comments, Opinions and Experiences About the Kock Internal Reservoir Ileostomy Procedure", O. H. Beahrs, M.D., *OSTOMY QUARTERLY*/Fall 1975.

"Intra-abdominal 'Reservoir' in Patients with Permanent Ileostomy", Nils G. Kock, M.D., *Arch Surg*/vol. 99, Aug. 1969.

"Present Status of the Continent Ileostomy: Experience at the General Infirmary, Leeds", *Div. Col. & Rect.*, Apr. 1976, vol. 19, No. 3, pp. 195-212.

"A Continent Colostomy: The Magetic Stoma Cap", Bauer et al., *The American Journal of Surgery*, vol. 134, Sep. 1977.

"A Continent Colostomy: The Magnetic Stoma Cap", Bauer et al., *Ostomy Quarterly*/Spring 1977.

"Rare Earth Cobalt Magnets in Modern Medicine", Hennig et al., 1974.

"The Quality of Life After Proctocolectomy and Ileostomy: A Study of Patients With Conventional Ileostomies Converted to Continent Ileostomies", Kock et al., *Div. Col. & Rect.*, May-Jun. 1974.

Literature relating to Angelchik, Anti-Reflux Prosthesis.

DL 137-668, Abstract, Stainless steel or plastics colostomy restrictor.

842,631, Abstract, Ostomy bag flanged connector.

GB 021767, Abstract, Non-irritating stoma bag sealing or closing material.

BE 859625, Abstract, Sealing plug for skin opening.

US 969488, Abstract, Non-clogging drain for surgical use.

BE 74-104, Abstract, Artificial anus valves of partially magnetic rubber components.

GB 030349, Abstract, External colostomy bag formed to prevent inflation.

DT 2929-246, Abstract, Small Calibre vessel prosthesis prodn.

GB 022776, Abstract, Plastics fastener for colostomy pouch.

*Primary Examiner*—Dalton L. Truluck
*Attorney, Agent, or Firm*—Antonelli, Terry & Wands

[57] ABSTRACT

A stoma control device and method are disclosed. The device comprises, in combination, a support such as a ring for surgical implantation in the body beneath the abdominal wall and substantially around the emerging bowel of a stoma, the support being formed of a relatively soft material such as soft plastic and having an inner surface which tapers outwardly to present a relatively large supporting surface for the bowel, and a plug adapted to be received in the stoma and within the bowel for controlling the stoma, the plug including an inflatable balloon, the balloon, on inflation, presenting an outwardly tapered surface with a shape which complements the tapered inner surface of the support whereby during control of the stoma with the device a relatively large surface of the bowel may be greatly compressed between the plug and the support so as to minimize pressure and tissue destruction.

23 Claims, 7 Drawing Figures

STOMA CONTROL DEVICE AND METHOD

BACKGROUND AND SUMMARY OF THE INVENTION

The present invention relates to a stoma device and method which provide control over the discharge from a person's stoma.

The United Colostomy Association estimates that there are approximately one million people in the United States and Canada with stomas. Many of these people woule like to have the same control over gas and feces that a normal rectal sphincter affords. Numerous devices and methods have been proposed in an attempt to provide a solution to this problem, for example, the magnetic cap arrangement disclosed in U.S. Pat. No. 3,952,726, the spherical balloon type device disclosed in U.S. Pat. No. 2,564,399 and the annular closure disclosed in German Offenlegungsschrift No. 2,558,521. However, to date no stoma device or method has been able to accomplish the desired control over gas and feces that a normal rectal sphincter affords without posing serious problems, the most significant of which have been tissue destruction and discomfort. More specifically, such known devices and methods may be problematical because, for example, they require undue distension of the bowel, they place relatively high and potentially harmful pressure on the abdominal wall and/or the bowel, and because they must be dimensioned in length, for example, within relatively small tolerances to achieve control or closure of a stoma.

An object of the present invention is to provide a stoma control device and method which avoid the aforementioned disadvantages of the known devices. More particularly, an object of the present invention is to provide a stoma control device and method which provide continence and which do so with patient comfort as well as the absence of tissue damage. Further objects of the present invention include the provision of a stoma control device and method which do not require undue distension of the bowel, and which do not place relatively high and potentially harmful stresses on the abdominal wall or on the bowel, and wherein the length or dimensional tolerances for closure or control of a stoma are somewhat forgiving.

The above and other objects of the invention are attained by providing a stoma control device comprising, in combination, a support means for surgical implantation in the body beneath the abdominal wall and at least substantially around the emerging bowel of the stoma, the support means having an inner surface which is positioned adjacent the bowel on implantation, at least a portion of the inner surface being tapered outwardly, and plug means adapted to be received in the stoma and within the bowel, the plug including expandable means which, on expansion, presents an outer surface at least a portion of which is outwardly tapered with a shape which complements the outwardly tapered surface of the support means whereby during control of the stoma with the device a relatively large surface of the bowel may be gently compressed between the respective tapered surfaces of the plug means and the support means so as to minimize pressure and tissue destruction.

The outwardly tapered portion of the inner surface of the support means preferably extends over at least a major portion of the length of the support means and, according to a preferred embodiment of the invention disclosed herein, this outwardly tapered portion of the inner surface extends over substantially the entire length of the support means. This provides a relatively large supporting surface for the bowel. The area of the outwardly tapered portion of the inner surface of the support means is preferably at least approximately one and one-half times the minimum cross sectional area of the bowel supported thereon during control of the stoma with the device.

The outwardly tapered portion of the outer surface of the expandable means is preferably substantially equal in length or co-extensive with the outwardly tapered portion of the inner surface of the support means so that with the support means as referred to above, the bowel is compressed over at least a major portion of the length of the support means or, as in the disclosed embodiment, over substantially the entire length of the support means during control of the stoma with the device. Preferably the area of bowel compressed during control of the stoma with the device is at least approximately one and one-half times the minimum cross sectional area of the bowel compressed between the support means and the expandable means.

According to further features of the present invention, the plug means includes an outwardly directed flange adjacent one end and the expandable means adjacent the other end. In the disclosed embodiment of the invention the expandable means is an inflatable balloon. The plug means includes a valve means for inflation and deflation of the balloon, an air passage being provided in the plug means to communicate the balloon with the valve means. According to the disclosed embodiment of the invention, the valve means is in the form of a nipple valve which accepts a syringe for inflation and deflation of the balloon.

A further feature of the invention is that the expandable means is dimensioned such that during control of the stoma with the device preferably at least a major portion of the expandable means is positioned radially inwardly of the support means. In the disclosed embodiment of the invention, the expandable means is dimensioned such that during control of the stoma substantially all of the expandable means is positioned radially inwardly of the support means. Thus, on expansion of the expandable means the outwardly tapered portion of the outer surface of the expandable means moves radially outwardly to gently compress the bowel against the outwardly tapered surface of the support means. Such movement produces a wedging action of the plug means within the bowel and support means to seal or close the bowel or stoma and to prevent explusion of the plug means from the pressue within the bowel. Because the force necessary to create this wedging action and seal or closure of the bowel or stoma is distributed over a relative large surface of the bowel between the respective tapered surfaces of the plug means and the support means, the bowel need only be gently compressed during control or closure of the stoma with the device thereby minimizing pressure and tissue destruction.

The support means of the invention is formed of a relatively soft material such as a soft plastic. A medical grade silicone elastomer may be used. In one form of the invention the support means is a ring having a continuous circular form. According to another form of the invention the support means is a ring which is broken so as to allow placement around the bowel.

In the disclosed embodiment of the invention the respective tapered surfaces of the support means and the plug means have a linear taper and are in the form of truncated cones.

The method of controlling a stoma according to the present invention comprises surgically implanting a support means of the aforementioned type in the body beneath the abdominal wall and at least substantially around the emerging bowel of a stoma, inserting a plug means of the aforementioned type in the stoma and within the bowel, and expanding the expandable means to gently compress a relatively large surface of the bowel between the respective tapered surfaces of the plug means and the support means whereby pressure and tissue destruction are minimized during control of the stoma.

BRIEF DESCRIPTION OF THE DRAWINGS

These and other objects, features and advantages of the present invention will become more apparent from the following description when taken in connection with the accompanying drawings which show, for purposes of illustration only, one preferred embodiment in accordance with the present invention and wherein.

DETAILED DESCRIPTION OF THE INVENTION

Figure 1:
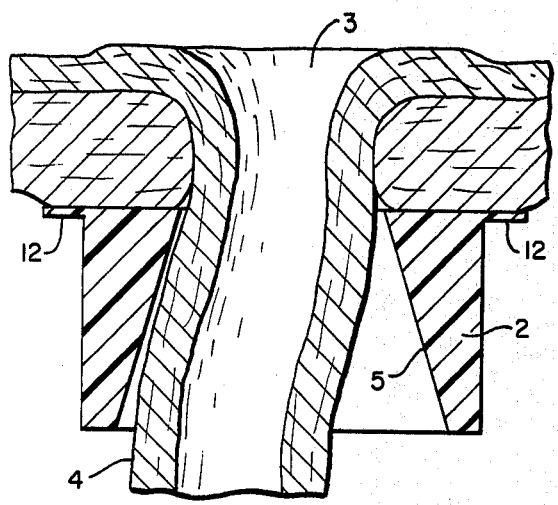
FIG. 1 is a cross-sectional view through a portion of the abdomen of a patient showing the position of a support means in the form of a ring according to the present invention in relation to the bowel and abdominal wall.

The stoma control device 1 illustrated in the application drawings comprises, in combination, support means in the form of a ring 2 for surgical implantation in the body beneath the abdominal wall 13 and around the emerging bowel 4 of a stoma 3, and a plug means or device 6 which is adapted to be received in the stoma and within the bowel 4 for controlling the stoma.

Figure 2:
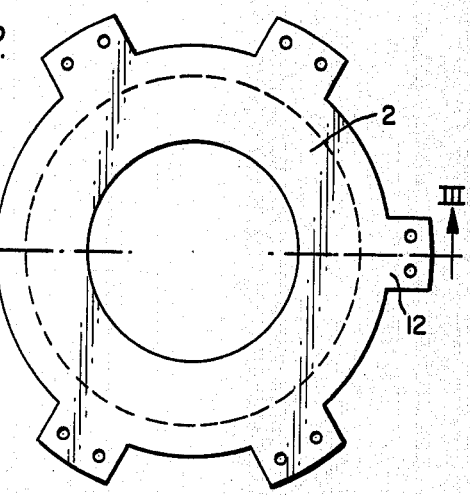
FIG. 2 is a top view of the support means or ring as shown in FIG. 1 showing perforated suture tabs on the outer periphery of the ring.
Figure 3:
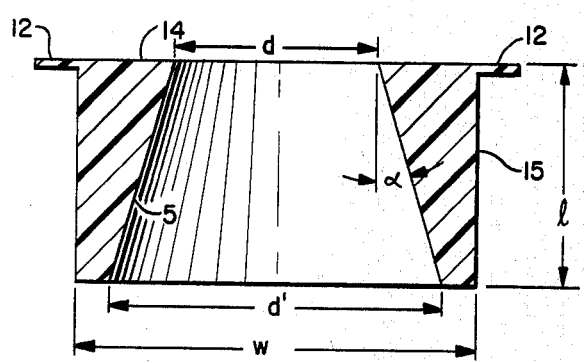
FIG. 3 is a cross-sectional view of the ring according to FIG. 2 as taken along the line III—III.
Figure 6:
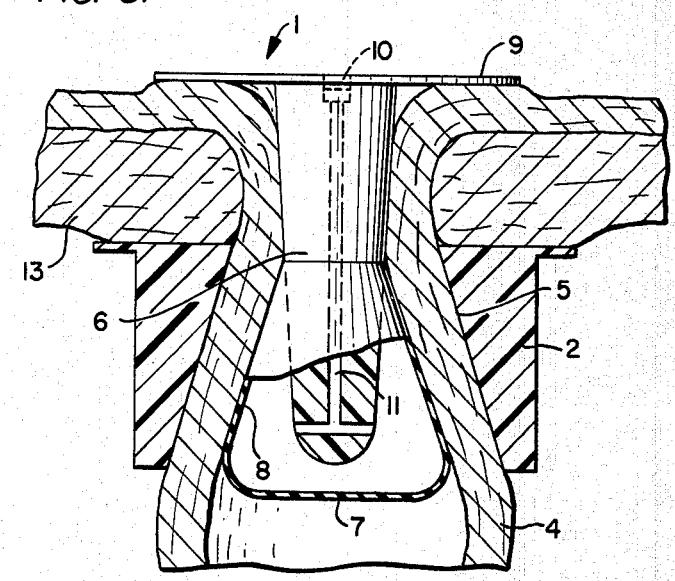
FIG. 6 is a cross-sectional view of a stoma control device according to the present invention in the assembled condition in the abdomen of a patient.

FIGS. 1 and 6 illustrate the ring 2 in place in the body beneath the abdominal wall 13 and around the emerging bowel 4 of stoma 3. The ring is circular in shape and is fastened securely to the abdominal wall 13 and adjacent the bowel by sutures at a plurality of perforated suture tabs 12 provided on the end or top surface 14 of the inner wall of the ring as shown in FIG. 2. The outer surface 15 of the ring 2 is perpendicular to the surface 14 of the ring which is positioned adjacent the abdominal wall 13 while the radially inwardly directed inner surface 5 of the ring tapers outwardly over the length of the ring, that is, from top to bottom, to present a relatively large supporting surface for the bowel 4.

In the illustrated embodiment, the ring 2 has a width w of 7.8 cm. and a length 1 of 4.0 cm. The inner surface 5 of the ring is outwardly tapered over the entire length of the ring. The taper is linear and at an angle $\alpha$ of 17° with respect to the longitudinal axis of the ring. Thus, the tapered inner surface 5 of the ring defines an opening through which the bowel 4 passes, where the cross sectional area of the opening increases in a direction into the stoma over the entire length of the ring. The opening has diameter d of 4.0 cm. at the top of the ring and a diameter d' of 6.6 cm. at the bottom. With such a configuration, the area of the tapered inner surface 5 of the ring is approximately 75 square cm. This area is several times the minimum cross sectional area of the bowel supported on the surface 5 during control of the stoma with the device. However, the area of the tapered inner surface 5 need not be this great but is preferably at least approximately one and one-half times the minimum cross sectional area of the bowel supported on the surface during control of the stoma with the device.

The support means or ring 2 should be formed of a soft plastic or rubber which is compatible with the human body. For example, a silicone material may be used such as a medical grade silicone elastomer manufactured by the Dow Chemical Company and sold under the trade name "Silastic". The ring is yieldable or resilient but preferably with a shape retaining character. It is envisioned that the ring may be either a solid material such as a solid plastic or a gel filled skin or membrane as commonly used in surgical implants, e.g. breast protheses. However, since the ring is to be permanently implanted for the patient's lifetime in case of permanent stomas, a solid construction is preferable so as to avoid the possibility of leakage of gel filling into the abdominal cavity.

The ring may have a continuous circular form as shown in FIG. 2 or may be broken so as to allow placement around the bowel rather than requiring the bowel to be drawn through the ring. It is preferable to provide the ring in a variety of circumferential sizes and lengths to accommodate the range of sizes of bowel, e.g. colon, ileum or other tissue conduit. Also, the angle of taper $\alpha$ of the surface 5 may be less than 17° as in the illustrated embodiment but should be sufficient to obtain the necessary wedging action between the plug device 6 and the ring to seal or close the stoma and prevent explusion of the plug device by pressures within the bowel. The angle of taper $\alpha$ may also be greater than that in the example but is preferably less than approximately 45° to 50°.

Figure 7:
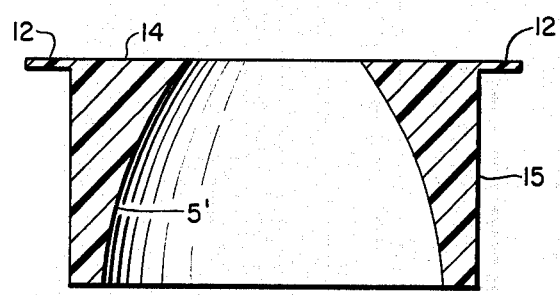
FIG. 7 is a cross-sectional view of another form of a ring according to the invention wherein the outwardly tapered inner surface is curvilinear.

In the illustrated embodiment of the invention, the taper of the surface 5 is linear. This is particularly advantageous in that with a similar or a like shaped outer surface on the balloon 7 of the plug device, the length requirements of the plug device are somewhat forgiving since with slight changes in the relative position of the surface 5 and balloon 7, the balloon can be inflated more or less and still compress the bowel against the surface 5 over a relatively large area. However, according to another form of the invention as illustrated in FIG. 7, the taper of the inner surface 5' may be curvilinear. The use of such a configuration provides a slightly greater support surface for the bowel for a ring or support means of a given length.

The area of the bowel compressed during control of the stoma is several times the minimum cross sectional area of the bowel supported on the surface 5 during control of the stoma with the device in the disclosed embodiment. While the area of bowel compressed need not be this great, it is preferred that the area of bowel compressed be at least approximately one and one-half times the minimum cross sectional area of the bowel compressed between the support means and the expandable means.

The plug 6 of the stoma closure device 1 is adapted to be received in the stoma 3 and includes an inflatable balloon 7. The balloon 7, on inflation, presents an outwardly tapered surface 8 with a shape which complements the tapered inner surface of the ring whereby during control of the stoma 3 a relatively large surface of the bowel 4 may be gently compressed between the ring and the plug so as to minimize pressure and tissue destruction. In the illustrated embodiment the balloon is outwardly tapered at substantially the same angle as surface 5, that is, 17°, and the surface 8 is substantially co-extensive with the surface 5 so that the bowel may be gently compressed over substantially the entire length of the ring.

Figure 4:
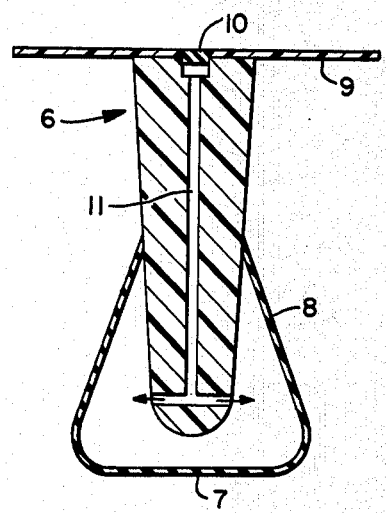
FIG. 4 is a cross-sectional view from the side of a plug according to the present invention and illustrating the balloon, plug body with flange and the passageway and valve for inflating and deflating the balloon with a syringe.
Figure 5:
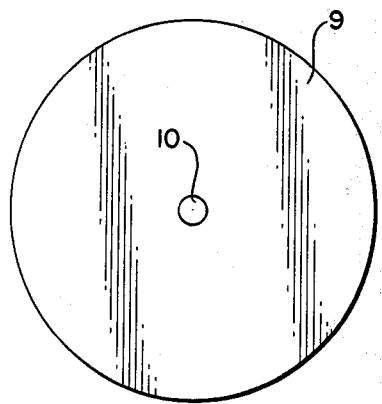
FIG. 5 is a top view of the plug of FIG. 4 schematically showing a female acceptor for a syringe for inflation and deflation of the balloon with air.

The plug 6 includes an outer flange 9 adjacent one end, the flange extending essentially perpendicularly to the longitudinal axis of the plug. In use, this flange makes contact with the outer skin of the patient's abdomen as shown in the drawings. The balloon 7 of the plug is located adjacent the other end of the plug 6. A valve 10, shown schematically in FIGS. 4 and 6 is provided in the plug 6 for inflation and deflation of the balloon 7. The valve may, for example, be a nipple valve which accepts a syringe for inflation and deflation of the balloon. An air passage or tubing 11 is provided in the plug between the balloon and the valve 10.

The flange or face plate 9 of the plug 6 in the illustrated embodiment is 7 cm. in diameter. The length of the plug is about 7 cm. This length includes a distal portion of approximately 4 cm. with the balloon and a proximal length to accommodate the thickness of the abdominal wall. Of course, these dimensions may vary from patient to patient depending on the size of the bowel, the thickness of the abdominal wall, etc. The diameter of the body portion of the plug will also vary for the same reasons as the diameter of the ring. This portion of the plug may be gently tapered as shown in FIGS. 4 and 6.

The materials of construction for the plug 6 are soft materials, such as a plastic or rubber, which are compatible with the human body. A medical grade silicone elastomer is one acceptable material. The balloon 7 should be readily collapsible on deflation and may be separately formed and attached to the plug 6 as by bonding or the balloon may be integrally formed, at least in part, with the plug 6 as will be readily apparent to the skilled artisan. The balloon may be conical in shape as shown in the drawings, that is with a tapered surface which is straight, or it may be formed with a curvilinear tapered surface such as an elliptically shaped surface. In any case the balloon, on inflation, should present an outwardly tapered surface with a shape which complements or substantially corresponds to the tapered inner surface of the support means or ring whereby during control of a stoma a relatively large surface of the bowel may be gently compressed so as to minimize pressure and tissue destruction.

FIG. 6 of the application drawings shows the stoma control device 1 in the assembled or operative condition. That is, with the ring 2 surgically implanted in the abdomen as discussed above and with the plug 6 in place and its balloon 7 inflated so that the bowel or tissue conduit 4 is gently compressed and obstructed so as not to allow the passage of air or stool. Thus, in the operative condition shown in FIG. 6 the device effectively closes the opening of the stoma 3. The ring 2 with its tapered surface 5 ensures that the inflated balloon 7 and the remainder of the plug 6 are retained in place and not expelled from the bowel or tissue conduit 4. The balloon pressing on the tissue conduit supported against the tapered ring also results in a slight downward pull or tensioning of the plug 6 such that the flange or face plate hugs the abdomen about the stoma and remains essentially flush therewith. When gas or stool builds up, the patient can deflate the balloon in a bathroom, remove the plug and expel the stool or gas.

By forming a stoma control device in the above manner, wherein a component or components are constructed out of soft materials such as soft plastic, wherein there is created a snug and tapered obstruction, and wherein a large surface of bowel is used in compression so as to minimize pressure and therefore tissue destruction, an improved stoma control device is attained. In particular, the device of the present invention provides continence, that is, control over gas and feces while avoiding the aforementioned problems which may occur with known devices. When properly positioned in place in a stoma the device is also essentially flush with the outer skin of the patient's abdomen thus enabling the patient to wear close fitting clothing without embarrassment and minimizing the intrusion upon the patient's freedom of movement.

The method of controlling a stoma according to the present invention comprises the steps of surgically implanting a support means of the aforementioned type, inserting a plug means of the type described in the stoma and within the bowel of the stoma, and expanding the expandable means of the plug means to gently compress a relatively large surface of the bowel between the respective tapered surfaces of the plug means and the support means whereby control of the stoma can be attained while minimizing pressure and tissue destruction.

While I have shown and described only one embodiment in accordance with the present invention, it is understood that the same is not limited thereto, but is susceptible to numerous changes and modifications as known to those skilled in the art, and I therefore do not wish to be limited to the details shown and described herein, but intend to cover all such changes and modifications as are encompassed by the scope of the appended claims.

I claim:

1. A stoma control device comprising, in combination, support means for surgical implantation in the body beneath the abdominal wall and at least substantially around the emerging bowel of a stoma, said support means being adapted to be fastened securely to the abdominal wall and to extend a predetermined distance along said bowel, and said support means including an at least substantially continuous inner wall means having an inner surface which is positioned adjacent said bowel on implantation and which is tapered outwardly along at least most of the length of said support means, and said support means having an end surface for positioning adjacent the abdominal wall, and plug means adapted to be received in said stoma and within said bowel, said plug means including outwardly directed flange means adjacent one end for cooperation with the outer surface of the body about the stoma and expandable means adjacent the other end, said expandable means, on expansion, presenting an outer surface which is outwardly tapered with a shape which complements the outwardly tapered inner surface of said support means over at least most of the length of said support means whereby during control of the stoma with said device a relatively large surface of the bowel may be gently compressed between the respective tapered surfaces of the plug means and the support means so as to minimize pressure and tissue destruction and to produce a wedging action of the plug means within the bowel and support means to close the stoma and to prevent expulsion of the plug means from pressure within the bowel.

2. A stoma control device according to claim 1, wherein the outer surface of said expandable means is outwardly tapered over essentially the entire length of said expandable means.

3. A stoma control device according to claim 1, wherein the inner surface of said support means taper outwardly over substantially the entire length of said support means.

4. A stoma control device according to claim 1, wherein the area of the outwardly tapered portion of the inner surface of said support means is at least approximately one and one-half times the minimum cross sectional area of the bowel supported on said outwardly tapered portion of the inner surface during control of said stoma with the device.

5. A stoma control device according to claim 1, wherein the respective tapered surfaces of the plug means and the support means are approximately the same length.

6. A stoma control device according to claim 1, wherein said expandable means is an inflatable balloon.

7. A stoma control device according to claim 6, wherein said plug means includes means permitting inflation and deflation of said balloon, air passage means being provided in said plug means between said balloon and said means permitting inflation and deflation.

8. A stoma control device according to claim 7, wherein said means permitting inflation and deflation accepts a syringe for inflation and deflation of said balloon.

9. A stoma control device according to claim 1, wherein the length of the expandable means is less than or approximately equal to the length of said support means so that at least most of the expandable means can be positioned radially inwardly of the support means during control of the stoma with said device.

10. A stoma control device according to claim 1 or 3, wherein the length of the expandable means is substantially the same as the length of said support means so that substantially all of the expandable means can be positioned radially inwardly of the support means during control of the stoma with said device.

11. A stoma control device according to claim 1, wherein said support means is formed of a relatively soft material.

12. A stoma control device according to claim 11, wherein said support means is formed of a soft plastic.

13. A stoma control device according to claim 12, wherein said support means is formed of silicone.

14. A stoma control device according to claim 12, wherein said support means contains silicone gel.

15. A stoma control device according to claim 1, wherein said support means is a ring having a continuous circular form.

16. A stoma control device according to claim 1, wherein said support means is a ring which is broken so as to allow placement around the bowel.

17. A stoma control device according to claim 1, wherein the tapered surface of said support means is linear.

18. A stoma control device according to claim 1, wherein the tapered surface of said support means is curvilinear.

19. A stoma control device according to claim 1, wherein the respective tapered surfaces of the support means and the plug means are in the form of truncated cones.

20. A stoma control device according to claim 1, wherein said support means is a ring, said end surface of the support means ring for positioning adjacent the abdominal wall being provided on its outer perimeter with at least one perforated suture tab for securely fastening the support means to the abdominal wall of the body.

21. A stoma control device according to claim 1, wherein the tapers of the respective tapered surfaces are linear.

22. A stoma control device comprising, in combination, support means for surgical implantation in the body beneath the abdominal wall and at least substantially around the emerging bowel of a stoma, said support means being adapted to be fastened securely to the abdominal wall and to extend a predetermined distance along said bowel, and said support means including an at least substantially continuous inner wall means having an inner surface which is positioned adjacent said bowel on implantation and which defines an opening through which the bowel passes, the cross sectional area of said opening increasing in a direction into said stoma over at least most of the length of said support means, and said support means having an end surface for positioning adjacent the abdominal wall, and plug means adapted to be received in said stoma and within said bowel, said plug means including outwardly directed flange means adjacent one end for cooperation with the outer surface of the body about the stoma and expandable means adjacent the other end, said expandable means, on expansion, presenting an outer surface whose cross sectional area increases in a direction into said stoma over at least most of the length of said support means and in a manner similar to the increase in cross sectional area of said opening defined by said inner surface of the support means whereby during control of the stoma with said device a relatively large surface of the bowel may be gently compressed between the plug means and the support means so as to minimize pressure and tissue destruction and to produce a wedging action of the plug means within the bowel and support means to close the stoma and to prevent expulsion of the plug means from pressure within the bowel.

23. A method of controlling a stoma comprising the steps of surgically implanting a support means in the body beneath the abdominal wall and at least substantially around the emerging bowel of a stoma by securely fastening said support means to the abdominal wall, said support means including an at least substantially continuous inner wall means having an inner surface which is positioned adjacent the bowel, said inner surface being tapered outwardly along at least most of the length of said support means, and said support means having an end surface which is positioned adjacent the abdominal wall, inserting a plug means in said stoma and within said bowel, said plug means including outwardly directed flange means adjacent one end and expandable means adjacent the other end, said expandable means, on expansion, presenting an outer surface which is outwardly tapered with a shape which complements the outwardly tapered surface of the support means over at least most of the length of said support means, and expanding said expandable means to gently compress a relatively large surface of the bowel between the respective tapered surfaces of the plug means and the support means whereby pressure and tissue destruction are minimized during control of the stoma and a wedging action of the plug means within the bowel and support means is produced to close the stoma and prevent expulsion of the plug means from pressure within the bowel.

* * * * *